US006776158B1

(12) United States Patent
Anderson et al.

(10) Patent No.: US 6,776,158 B1
(45) Date of Patent: Aug. 17, 2004

(54) SYSTEM FOR ANESTHETIZING LABORATORY ANIMALS

(75) Inventors: Leslie B. Anderson, Easton, PA (US); Alexis Agelan, Philadelphia, PA (US); James Eldon, Barto, PA (US)

(73) Assignee: Euthanex Corporation, Bethlehem, PA (US)

( * ) Notice: Subject to any disclaimer, the term of this patent is extended or adjusted under 35 U.S.C. 154(b) by 142 days.

(21) Appl. No.: 10/201,848

(22) Filed: Jul. 23, 2002

Related U.S. Application Data

(60) Provisional application No. 60/308,036, filed on Jul. 26, 2001.

(51) Int. Cl.[7] .......................... A61M 16/00; A01K 1/03
(52) U.S. Cl. ............................ 128/203.12; 128/203.26; 119/416; 119/417; 119/418; 119/419; 119/420; 119/421
(58) Field of Search ....................... 128/203.12, 203.14, 128/203.17, 203.26, 202.16, 203.25, 205.26, 204.23; 600/21, 22; 119/416, 417, 418, 419, 420, 421

(56) References Cited

U.S. PATENT DOCUMENTS

| | | | | | |
|---|---|---|---|---|---|
| 3,367,308 | A | * | 2/1968 | Quattrone ................... | 119/420 |
| 3,557,785 | A | * | 1/1971 | McQueen .............. | 128/205.16 |
| 3,838,687 | A | * | 10/1974 | Mosher ................. | 128/200.11 |
| 3,851,645 | A | * | 12/1974 | Connel .................. | 128/203.25 |
| 4,034,753 | A | * | 7/1977 | Connel .................. | 128/203.19 |
| 4,231,362 | A | * | 11/1980 | Pearson et al. ........ | 128/205.15 |
| 4,332,244 | A | * | 6/1982 | Levy et al. ............ | 128/205.25 |
| 4,343,304 | A | * | 8/1982 | Hickmann ............. | 128/200.14 |
| 4,520,808 | A | * | 6/1985 | LaBauve ............... | 128/200.14 |
| 4,721,060 | A | * | 1/1988 | Cannon et al. ............. | 119/420 |
| 4,747,402 | A | * | 5/1988 | Reese et al. ........... | 128/204.21 |
| 4,787,382 | A | * | 11/1988 | Pekovic ................. | 128/203.25 |
| 4,941,431 | A | | 7/1990 | Anderson, deceased et al. | |
| 5,109,797 | A | * | 5/1992 | Briant et al. ................ | 119/420 |
| 5,297,502 | A | * | 3/1994 | Jaeger ........................ | 119/420 |
| 5,297,544 | A | * | 3/1994 | May et al. ............. | 128/202.22 |
| 5,590,651 | A | * | 1/1997 | Shaffer et al. .............. | 600/532 |
| 5,626,130 | A | * | 5/1997 | Vincent et al. ........ | 128/203.12 |
| 5,899,846 | A | * | 5/1999 | Sternberg et al. ............. | 600/21 |
| 6,412,550 | B1 | * | 7/2002 | McLaughlin ................ | 165/236 |
| 6,497,756 | B1 | * | 12/2002 | Curado et al. ............. | 96/117.5 |

OTHER PUBLICATIONS

Braintree Scientific, Inc., "Model 2000 Small Animal Ventilator by Hallowell EMC", website: http://braintreesci.com/ventilator.htm.

(List continued on next page.)

*Primary Examiner*—Henry Bennett
*Assistant Examiner*—Mital Patel
(74) *Attorney, Agent, or Firm*—Dann, Dorfman, Herrell and Skillman; Henry H. Skillman

(57) ABSTRACT

A method and apparatus for anesthetizing one or more laboratory animals is provided. An anesthetic component is introduced into a pressurized gas stream for delivery to laboratory animals. In one embodiment of the invention, a solo apparatus is used to administer anesthetic component to a single animal. The apparatus may also contain a host cage providing a group apparatus connected to the pressurized gas stream that permits administration of anesthesia to one or a group of animals simultaneously. One or more solo and/or group apparatuses may be used to administer anesthetic components to different animals at various dosages. The apparatus may also include a thermoregulatory system that transfers heat to animals as they receive anesthesia to control the animals' body temperature. In addition, the apparatus may include an exhaust system to remove contaminants from exhaust gases and to withdraw exhaust gases from the apparatus or apparatuses.

32 Claims, 15 Drawing Sheets

OTHER PUBLICATIONS

Braintree Scientific, Inc., "Anesthesia Work Station", website: http://www.braintreesci.com/Anesworkstation.htm.

Braintree Scientific, Inc., "Braintree Scientific Vaporizers", website: http://www.braintreesci.com/vaporizer.htm.

Braintree Scientific, Inc., "Gas Anesthetizing Box", website: http://www.braintreesci.com/AnesBox.htm.

OSHA: OSHA Method # 103, "Anesthetic Gases: Guidelines for Workplace Exposures", website: http://www.osha-slc.gov/dts/osta/anestheticgases/anesthetic_gases.html.

* cited by examiner

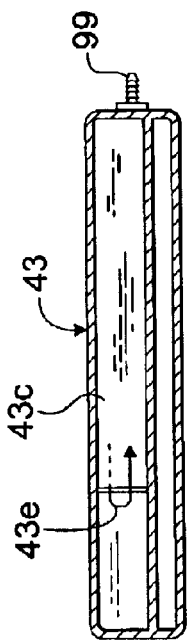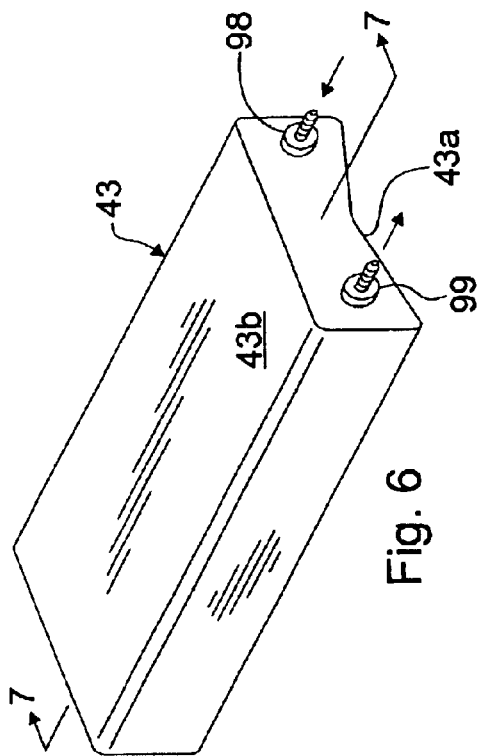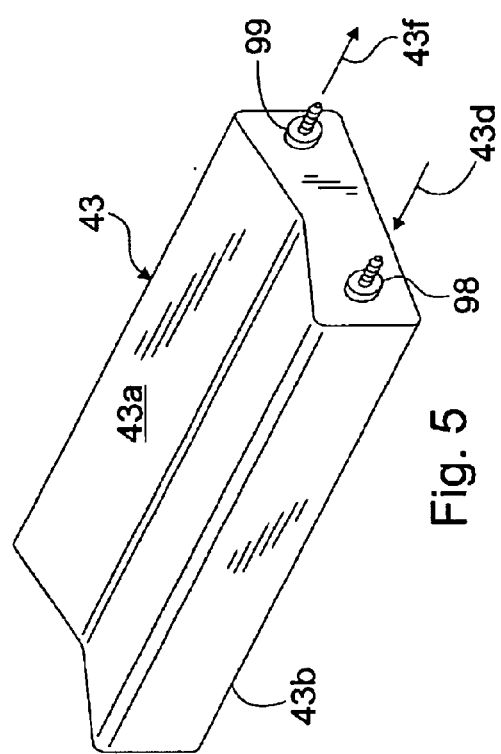

US 6,776,158 B1

SYSTEM FOR ANESTHETIZING LABORATORY ANIMALS

PRIORITY CLAIM

This application claims priority to U.S. Provisional Application No. 60/308,036, filed Jul. 26, 2001, which is hereby incorporated herein by reference.

FIELD OF INVENTION

The present invention relates to the administration of anesthesia to laboratory animals, and more particularly relates to a method and apparatus for safely and efficiently delivering gaseous anesthetic components to laboratory animals prior to and during laboratory procedures.

BACKGROUND OF THE INVENTION

Prior to the present invention, laboratory personnel had to devise their own systems to safely and efficiently anesthetize laboratory animals. Such self-devised systems frequently fail to administer gaseous anesthesia in a properly controlled fashion and therefore can lead to situations in which a laboratory animal receives either an insufficient amount of anesthetic or an overdose of anesthetic. In cases where a laboratory animal receives an insufficient amount of anesthetic, the under-anesthetized animal may suffer unnecessarily during a laboratory procedure, such as during a surgical procedure. In severe cases, the laboratory animal may become conscious during a surgical procedure, thereby jeopardizing its safety and the successful completion of the procedure. In case where a laboratory animal receives an overdose of anesthetic, the animal may take longer to recover from the procedure and, in the worst case scenario, may die as a result of a lethal overdose. Either of these situations would adversely influence the successful completion of the procedure.

Prior to the present invention, laboratory personnel would often deal with the inconvenience of working in a laboratory fume hood to prevent the accidental inhalation of anesthetic intended for the laboratory animal. Since laboratory fume hoods are generally not designed for working with laboratory animals, particularly when a procedure involves the simultaneous manipulation of several animals, use of conventional fume hoods may prove to be cumbersome.

Prior to the present invention, laboratory personnel had to devise their own systems for maintaining the normal body temperature of a laboratory animal before, during, and after an experimental procedure. If an experimental procedure requires surgery, then maintenance of a laboratory animal's normal body temperature is essential for the animal's survival. Loss of thermoregulatory homeostasis can lead to physiological shock, which is frequently fatal.

With the foregoing in mind, the present invention provides a method and apparatus for safely and efficiently delivering gaseous anesthetic components to laboratory animals prior to and during laboratory procedures. Moreover, it provides a method and apparatus wherein laboratory personnel can safely and efficiently perform multiple procedures simultaneously.

SUMMARY OF THE INVENTION

The present invention provides a method and apparatus for safely and efficiently anesthetizing laboratory animals prior to and during surgical procedures. Moreover, the invention enables laboratory personnel to perform multiple procedures on different animals simultaneously, thereby reducing the time required to accomplish these procedures. Portable components of the apparatus maximize the ease with which the apparatus can be used with other laboratory equipment. The present invention may be comprised of one or more components that may be selectively used to perform a variety of tests and procedures.

A gaseous anesthetic supply system may be provided, comprising a gas supply and a first regulator which provides means to control the flow rate of the gas stream. The gas supply may supply a stream of pure oxygen. The anesthetic supply system may further comprise a vaporizer which introduces anesthetic components into the incoming oxygen stream, and a second regulator which controls the flow rate of gaseous anesthetic/oxygen mix for delivery to a laboratory animal. Where it is desired to facilitate the rapid recovery of laboratory animals following anesthesia, the anesthetic gas stream may be altered or bypassed by an alternate gas to facilitate recovery of the animal. For example, the system may include an emergency bypass feature that substitutes pure oxygen for anesthetic gas mix.

Anesthetic gas or alternate gas streams may be delivered to the laboratory animal in multiple ways under the present invention. In one embodiment of the invention, gas is delivered directly to a laboratory animal using a delivery mask that conveys the gas stream to the nose of the animal. Gas may also be delivered to one or more laboratory animals by placing the animal or animals in an enclosed imperforate container or host cage and introducing the gas stream into the cage. Where delivery masks are used, the invention provides a variety of delivery masks designed to fit different animal species that are used in laboratory procedures. The delivery masks are configured to conform to the anatomy of the laboratory animal so that gas is delivered directly to the animal with minimal fugitive emissions of gas. By minimizing fugitive emissions of gas, the volume of gas consumed or wasted is reduced, and the risk of exposing lab personnel to gas emissions is lowered.

A thermoregulatory system may be provided to achieve and maintain a set temperature on the exterior of the animal supports where animals are positioned during procedures. By controlling the temperature of the animal supports, the body temperature of the laboratory animal may be maintained within a desired range to ensure the well-being of the animal and facilitate the successful completion of the procedure.

The present invention may further include an exhaust system that removes exhaled gases from the vicinity of the animal. The exhaust system may include filters, such as activated carbon filters, which capture exhaled gases and contaminants. The filters may be used in connection with delivery masks, host cages or other gas delivery mechanisms to capture exhausted gases and contaminants. This feature further minimizes inadvertent inhalation of exhaust gases by laboratory personnel. Filters may be used in conjunction with indicators or sensors that show the remaining absorptive capacity of the filters, signaling when the filter should be changed. In addition to or in lieu of filters, the exhaust system may also comprise a horizontal negative pressure recapture apparatus to vent exhaled gases and excess anesthetic, thereby ensuring the safety of laboratory personnel.

The anesthetizing system may be configured for use on a laboratory bench. Alternatively, the anesthetizing system may include portable components that permit the system to be easily transported and set up in different locations. In one portable system, anesthetic gas may be delivered through a check valve that opens to deliver gas as the animal inhales and closes when the animal exhales. Exhaled gas may be directed through a filter before being discharged. The gas may be delivered through a mask and air exchange chamber mounted adjacent to an animal support base. The support base may be connected to a thermoregulatory system to control the animal's body temperature.

BRIEF DESCRIPTION OF THE DRAWINGS

All of the objects of the invention are more fully set forth hereinafter with reference to the accompanying drawing, wherein:

FIG. 5 is an isolated view of the animal support of FIG. 4 showing a channeled surface on which a laboratory animal may be placed.

FIG. 6 is an isolated view of the animal support of FIG. 4 inverted relative to the position in FIG. 5 to illustrate a flat surface on which a laboratory animal may be placed.

FIG. 7 is a cross-sectional view of the animal support taken on the line 7—7 of FIG. 6;

DESCRIPTION OF THE PREFERRED EMBODIMENT

Figure 1:
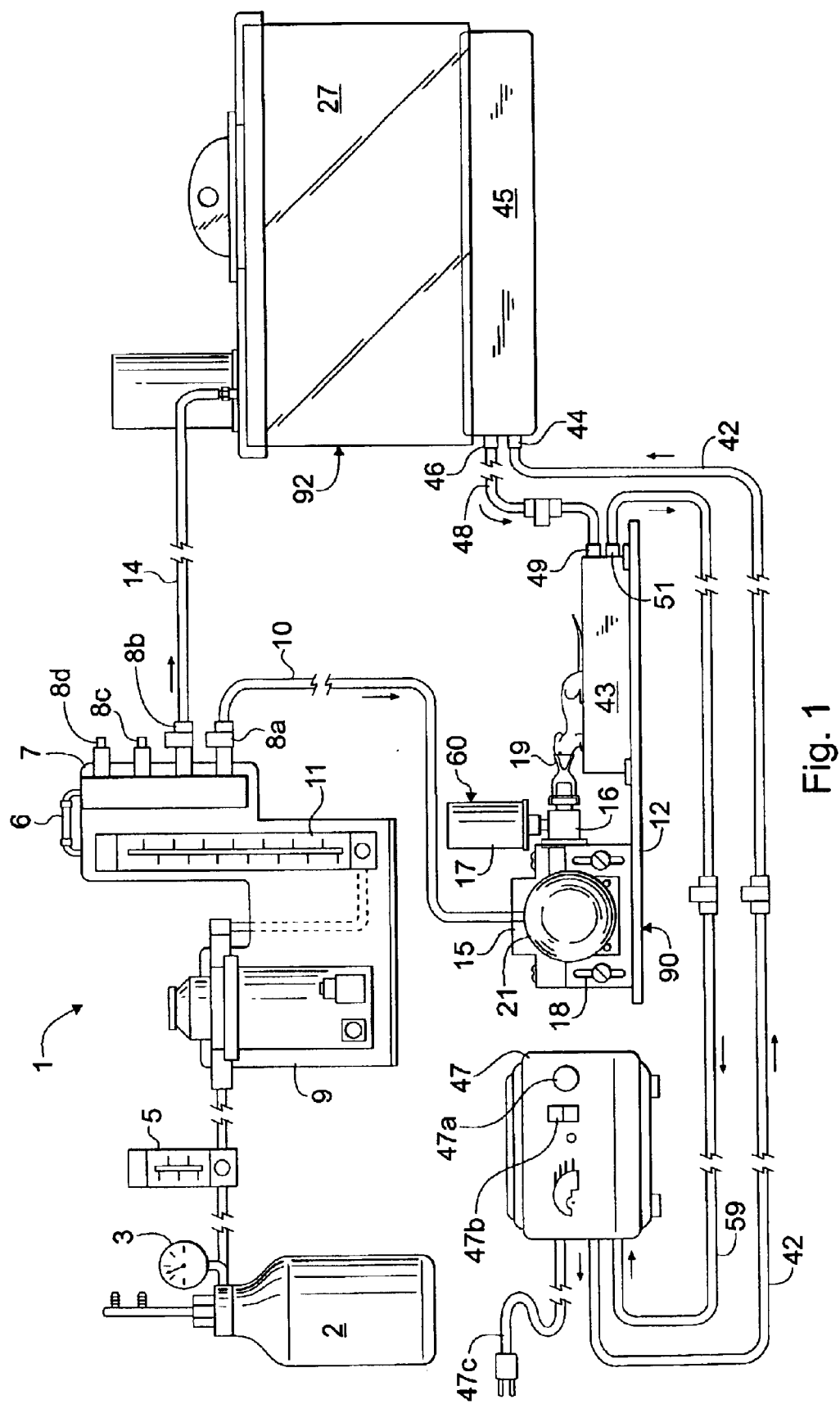
FIG. 1 is a diagrammatic view of a preferred apparatus embodying the present invention.

Referring to FIGS. 1–17 generally, and to FIG. 1 in particular, a system in accordance with the present invention is shown and designated generally as 1. The system 1 is particularly adapted for use in laboratories and research facilities in which tests and experiments are performed on animals that require the administration of anesthesia. Such tests and experiments must be performed on a properly anesthetized animal to facilitate successful completion of the procedure and ensure humane treatment of the animal during the procedure. The method and apparatus of the present invention provide means for the controlled delivery of gaseous components for inhalation by laboratory animals, and means for the removal of gases exhaled by the animals. The gaseous components are delivered in a carrier medium, such as pressurized air, oxygen gas, or the like, which is infused with atomized or vaporized anesthetic components. The flow of anesthetic components is controlled to achieve a concentration in the carrier medium that is sufficient to anesthetize a laboratory animal.

Figure 2:
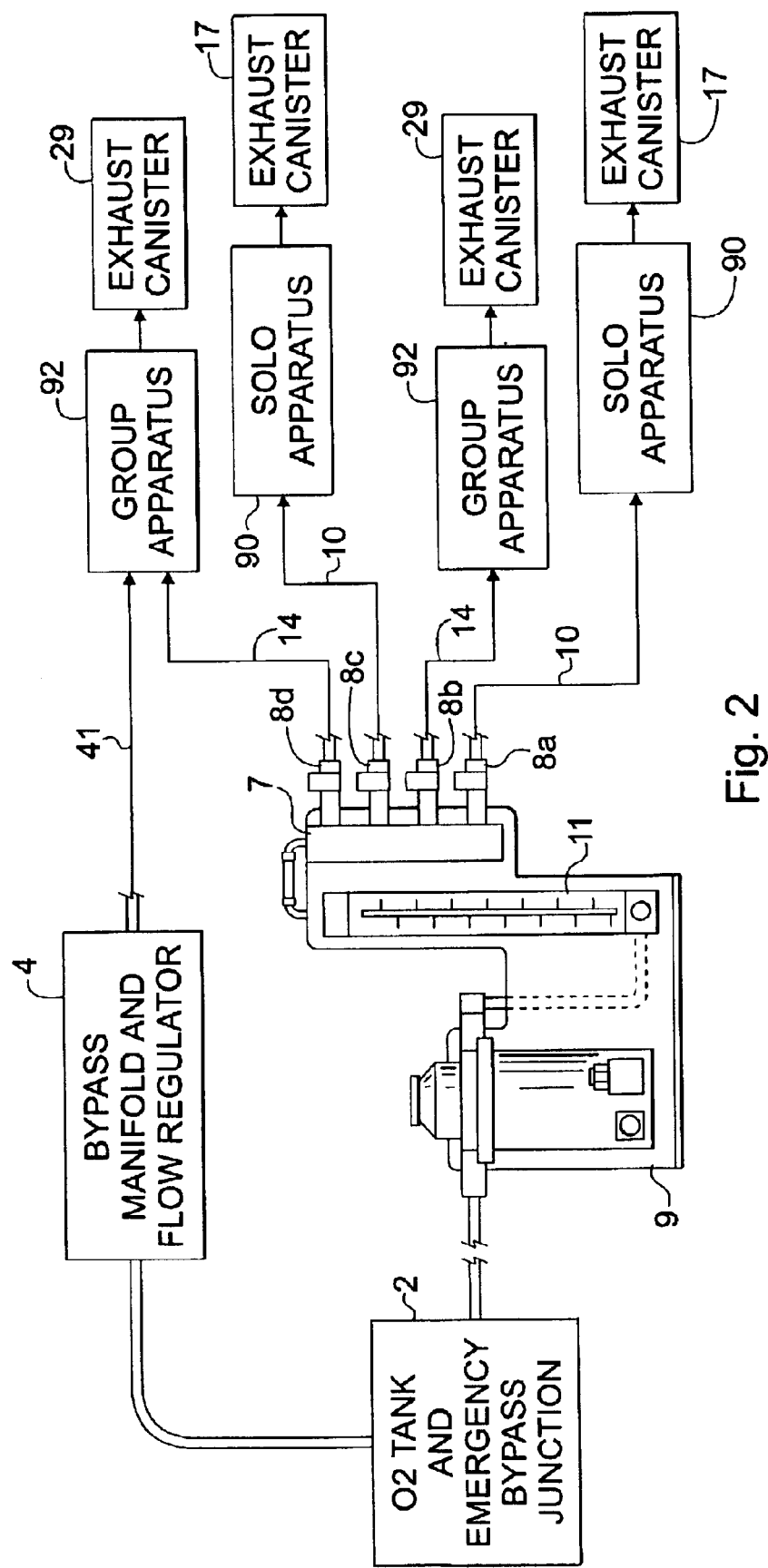
FIG. 2 is a schematic view and block diagram of a gaseous anesthetic system with outlets to an anesthesia support base and an anesthetic host cage as illustrated in FIG. 1.

The carrier gas is supplied to the system from a suitable source. Referring to FIGS. 1–2, the carrier gas is supplied from a pressurized gas tank 2 containing oxygen gas. The oxygen gas may be mixed with the anesthetic component in a life support system and supplied through a delivery system. Tank 2 is equipped with a oxygen pressure regulator 3 (for example, Euthanex Model #EZ-220 or EZ-230) to provide means to regulate the flow rate of oxygen leaving the tank and entering the system 1. The flow of the oxygen as it enters the system 1 is detected by a flow meter 5. The oxygen is delivered from flow meter 5 to a vaporizer 9, which atomizes components to facilitate their introduction into the incoming carrier stream. In accordance with the present invention, the system 1 may introduce one of a group of anesthetic components, including but not limited to, isoflurane, halothane, enflurane, and sevoflurane. Vaporizer 9 blends oxygen and anesthetic to a proper ratio and discharges the oxygen-anesthetic mixture to a flow meter 11. The vaporizer 9 has a large locking dial with gradations that may be adjusted to control the composition of the gaseous mixture. Flow meter 11 provides means to detect and regulate the flow rate of the anesthetic gas mix which exits vaporizer 9. The anesthetic gas mix is delivered to a gas manifold 7, which has a single inlet port for entry of anesthetic gases and a plurality of outlet ports for supplying the anesthetic gases to the anesthetic delivery system. In FIG. 1, the manifold 7 is shown with four outlet ports 8a–8d. Outlet port 8a is connected to a first apparatus 90, and outlet port 8b is connected to a second apparatus 92, as will be explained in more detail below.

The system of the present invention facilitates the simultaneous performance of a variety of different laboratory procedures. The components of the present invention allow for the administration of anesthetic to a single laboratory animal, or to a plurality of laboratory animals at one time. Referring to FIG. 2, the gas manifold 7 is shown connected to four apparatuses. The system 1 includes two solo apparatuses 90 and two group apparatuses 92. Each solo apparatus 90 is configured to administer anesthetic to a single animal. Each group apparatus 92 is configured to administer anesthetic to a plurality of animals simultaneously. Each apparatus discharges to an exhaust mechanism that captures anesthetic gas exhaled from the animals and any contaminants in the released gas. In FIG. 2, the solo apparatuses are shown discharging to exhaust canisters 17, and the group apparatuses are shown discharging to exhaust canisters 29.

Referring now to FIGS. 3–7, each solo apparatus 90 comprises an animal support base 43 which is configured to support a single laboratory animal during administration of an anesthetic. The base 43 may be formed with different dimensions and geometries depending on the particular species of animal used and the type of procedure being performed. In FIGS. 5–7, the base 43 is shown as a reversible structure having a channeled or depressed surface 43a on one side and a substantially uniform or flat surface 43b on the opposite side. The channeled surface 43a is configured to support a laboratory animal during non-surgical procedures and tests, and the flat surface 43b is configured to support an animal during surgical procedures and tests. In practice, the animal may be placed on the side 43b during performance of the procedure, and when the procedure is completed, the base 43 may be reversed to expose the channeled side 43a, and the channeled side will cradle the animal during recovery from anesthesia. The support base 43 may further include mechanisms for restraining the laboratory animal.

Referring to FIG. 1, the outlet port 8a on the gas manifold 7 is connected to a conduit 10 through which anesthetic gas mix is supplied to solo apparatus 90. Solo apparatus 90 comprises a breathing device 15 that delivers an anesthetic gas mix to a laboratory animal. The breathing device 15 has an internal air exchange chamber which receives anesthetic gas mix from the conduit 10. Preferably, anesthetic gas mix enters the chamber in a controlled manner that prevents harm to the animal and inadvertent release of excess anesthetic gas. For example, the anesthetic gas mix may enter the air exchange chamber through an inlet port and a check valve, such as a duck bill check valve. The check valve may facilitate controlled inflow of anesthetic gas mix into the air exchange chamber upon inhalation by the animal. Breathing device 15 may have automatic controls which can be programmed to deliver a specified flow rate of anesthetic gas mix appropriate for a specific laboratory animal. Breathing device 15 may also include a ventilator to assist the breathing process of a laboratory animal under conditions of deep anesthesia wherein the animal can no longer breathe without assistance. Breathing device 15 may further comprise a small soft chamber of bulb 21 which may be used to manually ventilate the respiratory system of a laboratory animal for the purposes of resuscitation.

Figure 15:
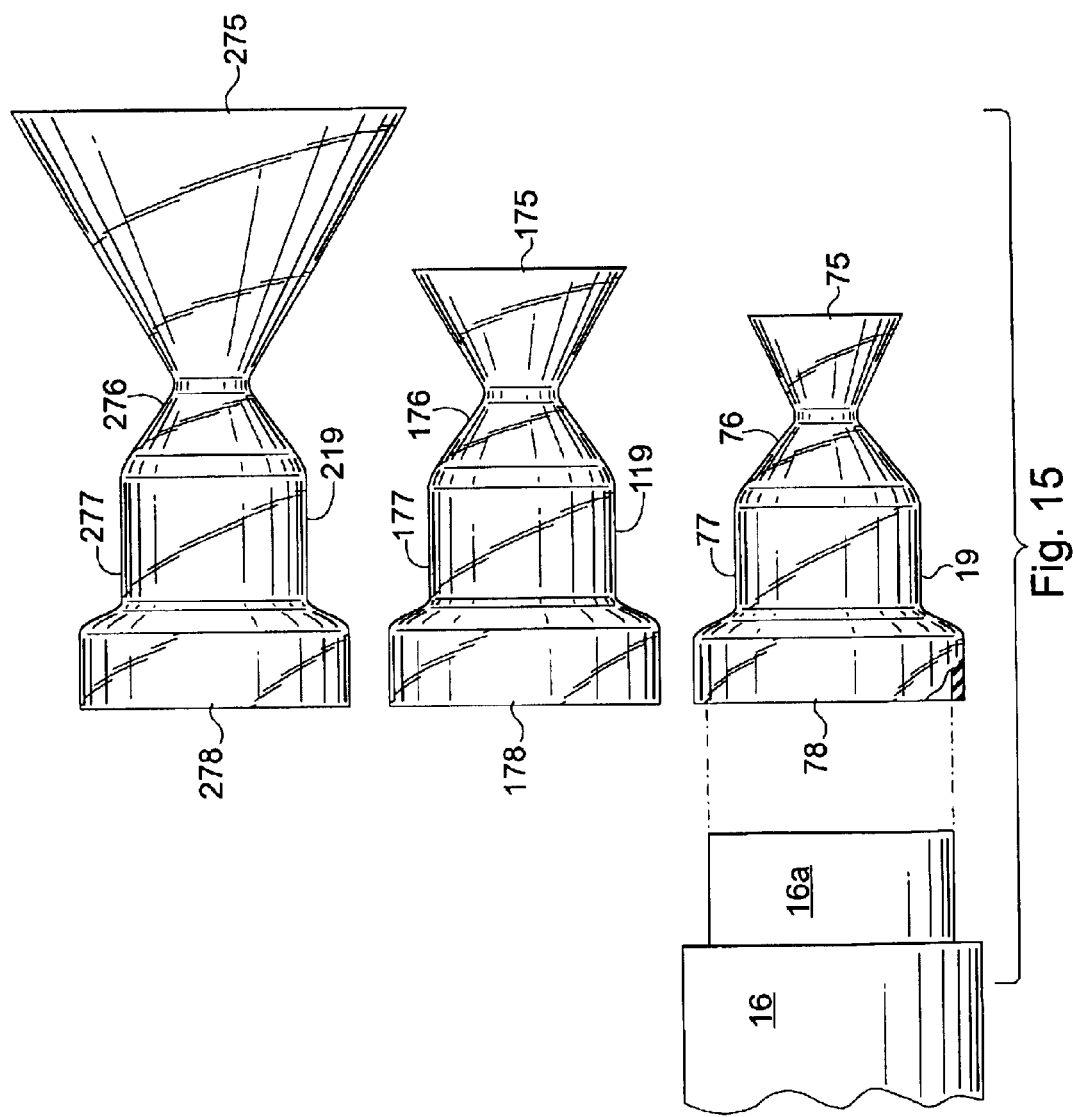
FIG. 15 is an elevational view of a set of gas delivery masks of the present invention.

The anesthetic gas mix enters the breathing device 15 and flows into an air exchange chamber 16 having a connector 16a (see FIG. 15) connected to a gas delivery mask 19. The mask 19 is configured to deliver anesthetic gas mix directly to the nose of a laboratory animal. Preferably, gas delivery masks 19 are produced in a plurality of sizes. Referring to FIG. 15, three masks 19, 119, and 219 are shown which are designed to deliver anesthetic gas mix to different species of laboratory animals. The features of the masks 19, 119 and 219 are essentially the same for each mask, although dimensions may vary to accommodate different animal species. For purposes of this description, the features of mask 19 will be described. The features of mask 119 are identified by reference numbers corresponding to the numbered features on mask 19, with the addition of 100. The features of mask 219 are identified by reference numbers corresponding to the numbered features on mask 19, with the addition of 200. The first end of the mask 19 is comprised of a cone-like enclosure 75 configured to fit around the nose of a laboratory animal. The anterior end of the animal may be placed adjacent to the mask such that the nose of the animal is disposed within the enclosure 75. The enclosure 75 converges to a small neck which connects to a sheath 76. The sheath 76 is a cone-shaped section having a small diameter end connected to the enclosure 75 and a wider diameter end. The small diameter end of sheath 76 converges toward the enclosure 75 so that gas flow is focused in a relatively narrow stream to the animal's nose. The wider diameter end of the sheath 76 connects to a cylindrical body section 77, which in turn connects to an enlarged diameter fitting 78 at the second end of the mask. The fitting 78 is configured to connect the mask 19 to the internal chamber of the breathing device 15 or other source of gas. The mask 19 may be connected to the gas source with any type of connection. For example, the interior of the second end of the fitting 78 may be slightly larger than the outer diameter of a connector 16a so that the mask is connected to a source of gas by frictional engagement of the second end of the fitting 78 with the connector 16a. Alternatively, the interior diameter of the second end of the fitting may contain female threading that cooperates and mates with complementary male threads on the exterior of the connector. The masks 19, 119 and 219 may be used to deliver anesthetic gas mix to various species, including but not limited to, rabbits, mice, rats, hamsters, guinea pigs, cats, small dogs, reptiles, and birds. The material used to form masks 19, 119 and 219 is preferably transparent so that the animal's breathing can be visually monitored. The interiors of the the second end of the fittings 78, 178 and 278 are of the same diameter so as to enable substitution of any one of the masks 19, 119 and 219 for another mask, as when the anesthesia system of the present invention is used for different species of laboratory animals. All of the masks are adapted to be mounted on the same connector 16a.

Figure 3:
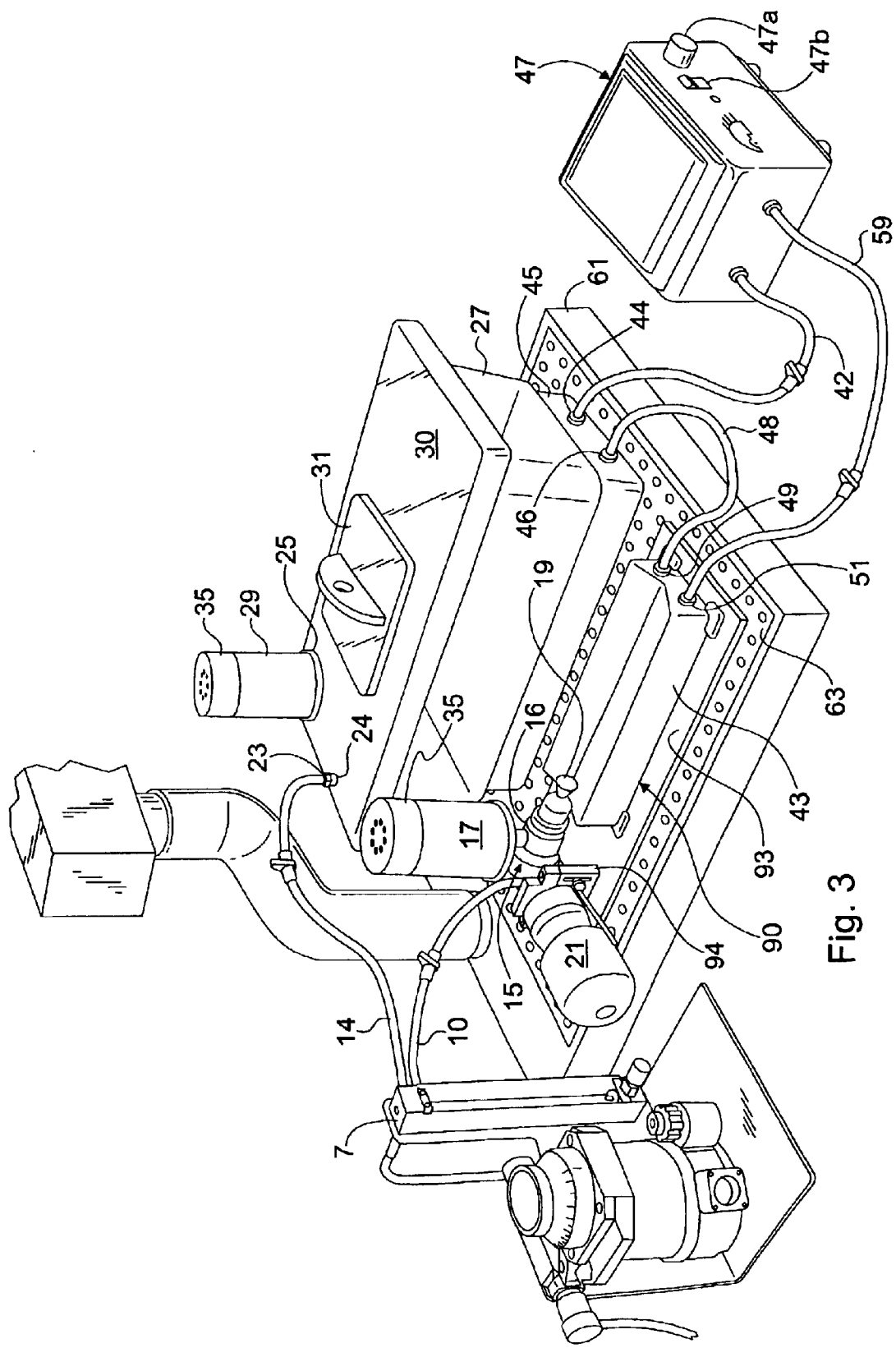
FIG. 3 is a perspective view of components of the gaseous anesthetic system, the anesthesia support base, the anesthetic host cage, an exhaust system, and a thermoregulatory system.
Figure 4:
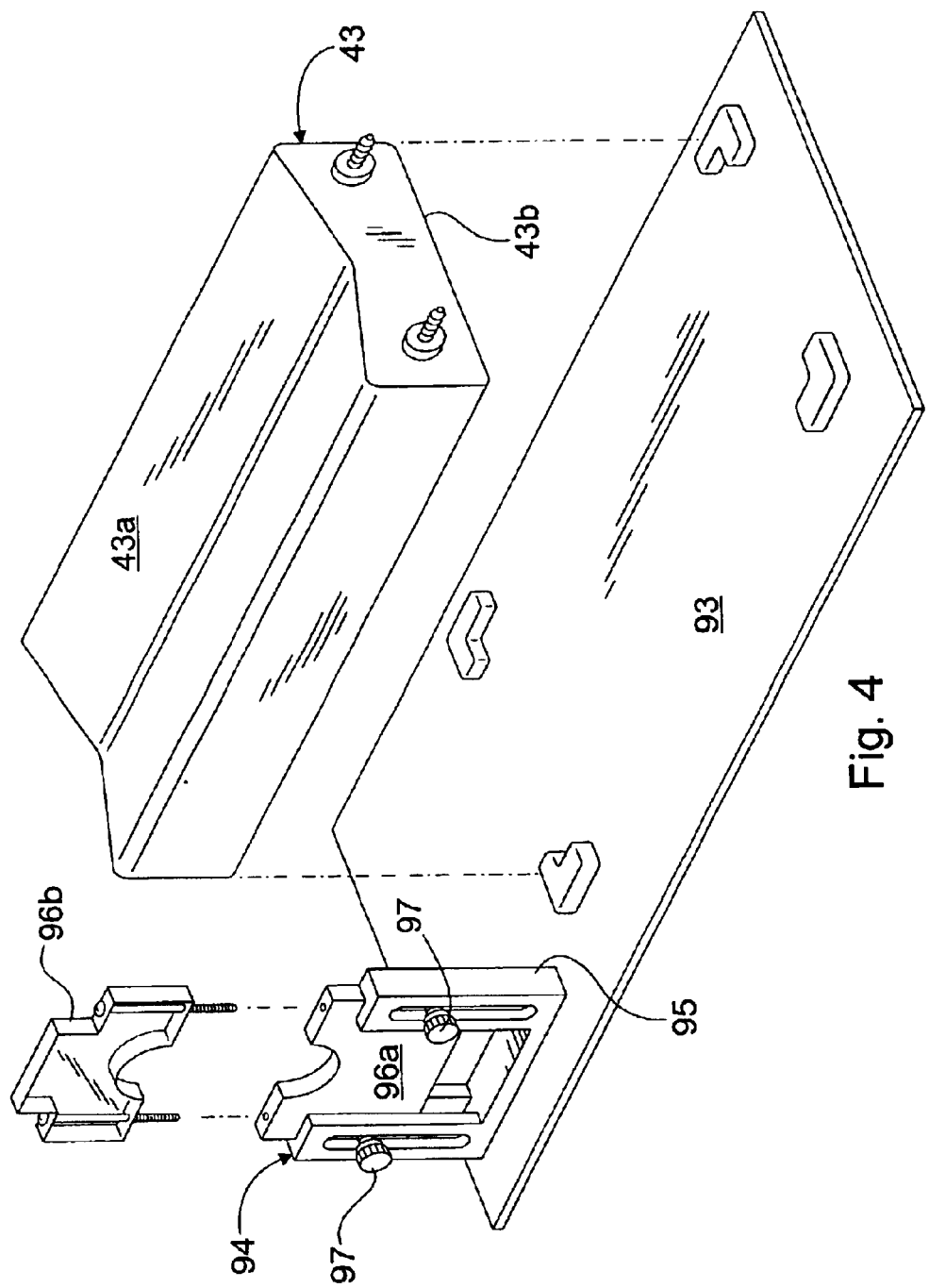
FIG. 4 is an exploded perspective view of a reversible animal support of the apparatus in FIG. 1.

Preferably, an adjustment mechanism 18 is provided to adjust the position of the gas delivery mask 19 relative to the support base 43. In this way, the mask 19 may be selectively positioned to accommodate a particular size of animal. Referring to FIGS. 3–4, the support base 43 is configured to rest on a animal support 93. The breathing device 15 cooperates with a clamp 94 mounted on the animal support 93. The clamp 94 includes an upright frame 95, a first plate 96a and a second plate 96b, as shown in FIG. 4. The plates 96a and 96b connect together, forming an interior aperture that fits around a portion of the breathing device 15. As such, the plates 96a and 96b may be connected to form a clamp around the breathing device. The plates 96a and 96b are configured to slide within the frame 95 when clamped around the breathing device 15 to adjust the position of the breathing device relative to the support base 43. A pair of thumb screws 97 extend through a pair of slots in the frame 95 and are configured to engage the first plate 96a to control the adjustment of the breathing device relative to the base 43. More specifically, the thumb screws 97 are configured to protrude into and out of engagement with the first plate 96a when the screws are tightened or loosened in the slots of the frame. In this way, the position of breathing device 15 relative to the base 43 may be adjusted by loosening the thumb screws 97 in the frame 95. The breathing device 15 may be locked into a fixed position by tightening the thumb screws 97 so that the screws engage the first plate 96a and limit further movement of the plates.

Gas delivery mask 19 is configured to minimize the distance, or "dead space", between a laboratory animal's nose and the gas supply line. More specifically, the delivery mask 19 is configured to cover only the nose of a laboratory animal, thereby facilitating inhalation of anesthetic gas mix. The delivery mask 19 does not cover the mouth of the animal, through which gases may be exhaled, so that exhaled gas is not released back into the mask. As a result, the potential for inadvertent euthanasia caused by inhalation of exhaled anesthetic gases and carbon dioxide is reduced. Since exhaled gas is not released back into the gas delivery mask, the masks of the present invention may be referred to as non-rebreathing gas delivery masks.

The non-rebreathing gas delivery masks described herein are preferably formed of a flexible plastic that conforms to the contours of an animal's nose, thereby providing a good seal to minimize the release of anesthetic gas mix into the environment. The breathing device 15 of the system may also include an intubating tube (not shown) which may connect to the connector 16a of the chamber 16 in place of the mask 78, and may be used as an alternative to a delivery mask to deliver gaseous anesthetic components directly into the lungs of a laboratory animal.

Referring to FIGS. 1 and 3, the solo apparatus 90 preferably includes an exhaust system 60 which captures gases exhaled by the laboratory animal. In this way, the risk of animal death due to inhalation of excess anesthetic or exhaled carbon dioxide is further minimized in the present invention. The exhaust system 60 may be comprised of an air filter 17 which is connected to an exhaust port in the chamber of the breathing device 15, and provides means to capture anesthetic gas contaminants, such as excess anesthetic gas mix and exhaled carbon dioxide, from the breathing device 15. The filter 17 contains an absorbent, such as charcoal, which provides means to capture anesthetic gas contaminants in the outflow of anesthetic gas mix.

Figure 8:
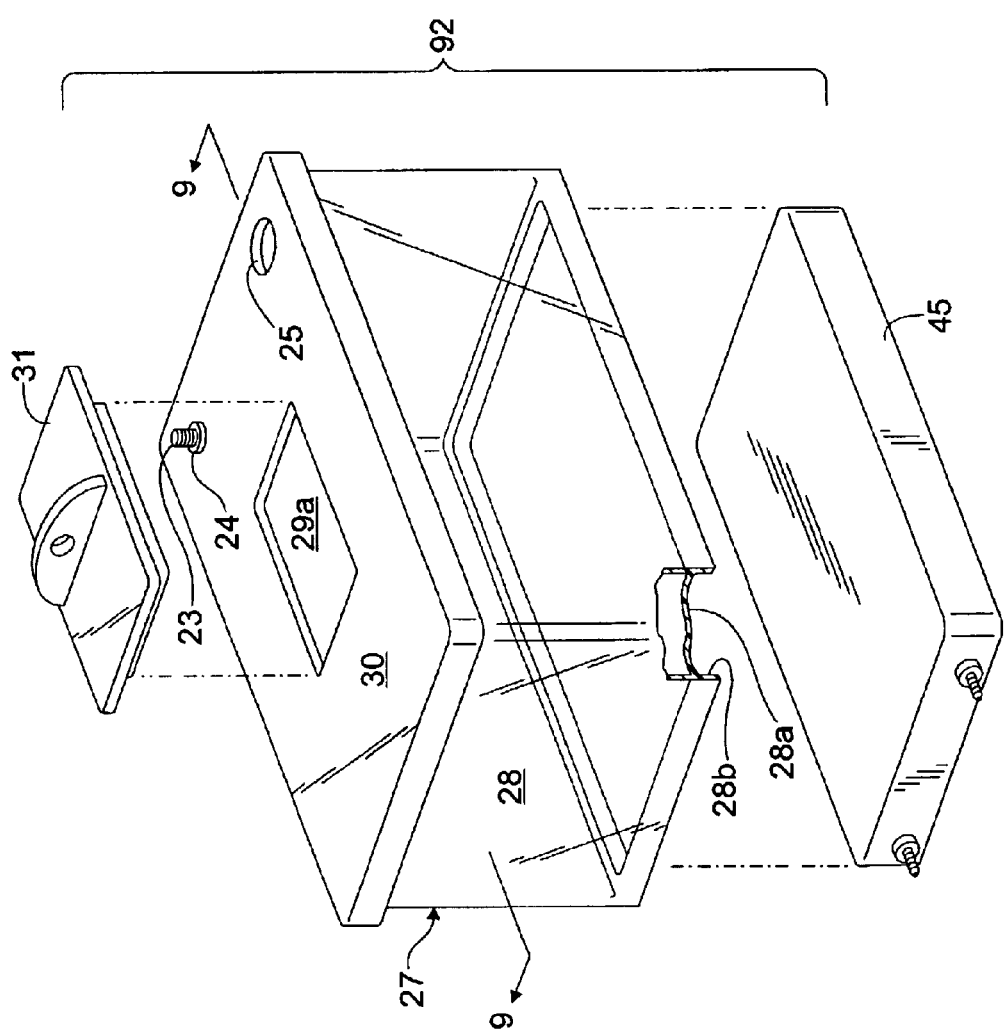
FIG. 8 is an exploded view of an anesthetic host cage and support base.
Figure 9:
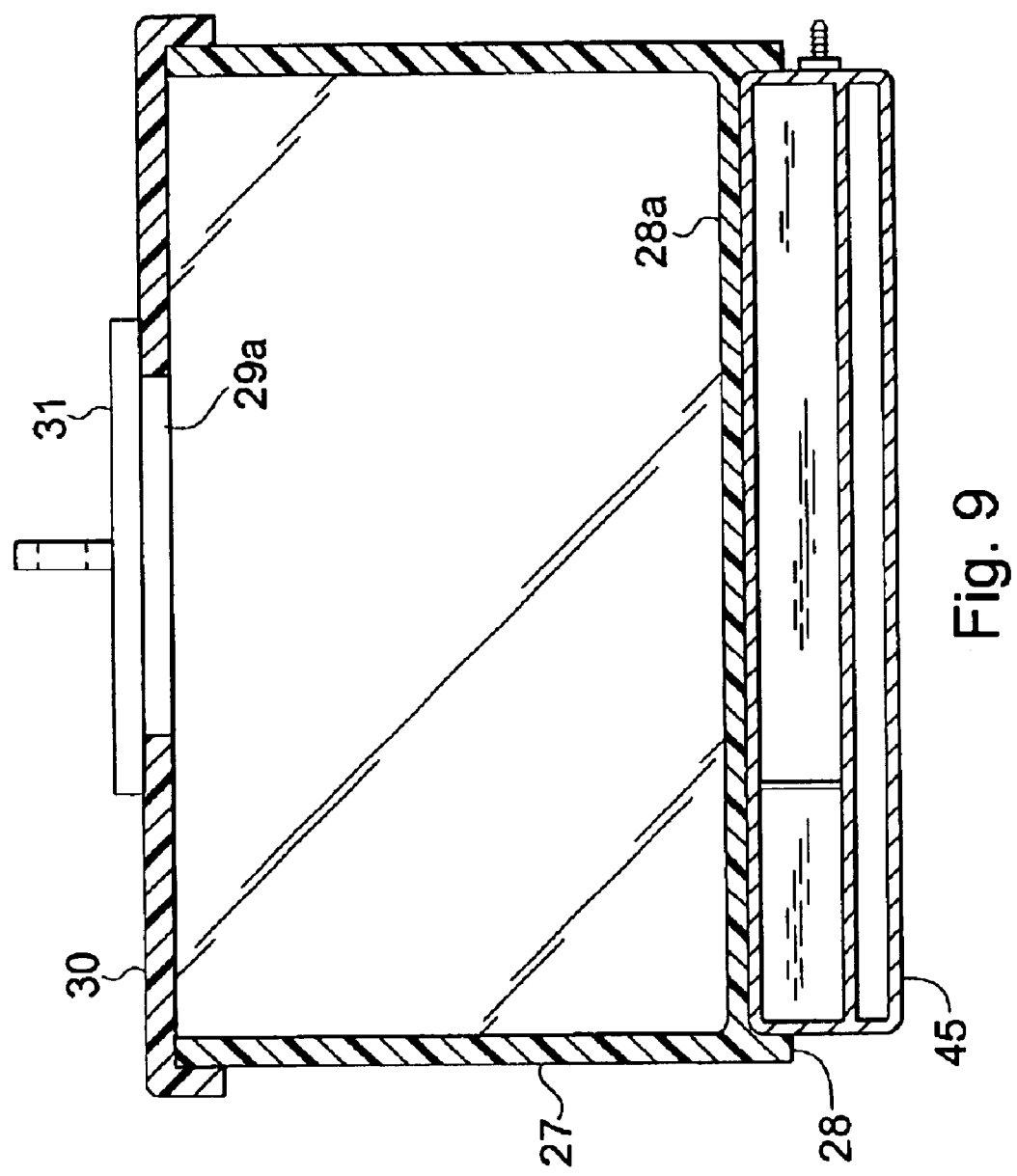
FIG. 9 is a cross-sectional view of the anesthetic host cage of FIG. 8 in an assembled condition.

The system 1 further comprises a group apparatus 92 for administering an anesthetic component to a plurality of animals. The outlet port 8b of gas manifold 7 is connected to a conduit 14, which provides means to deliver anesthetic gas mix to a group apparatus 92. The group apparatus 92 comprises anesthetic host cage 27 adapted to deliver anesthetic gas mix to a plurality of laboratory animals at one time. Referring to FIG. 8, anesthetic host cage 27 is shown as an imperforate container having sidewalls 28 that project downwardly below the bottom wall 28a to form an open bottom pocket 28b. The pocket 28b is configured to fit snugly over a bottom support base 45 to enable heat transfer from the base 45 to the bottom wall 28a. The cage 27 has a cover 30 configured to be placed over the sidewalls 28 to form an enclosure when the sidewalls are position on the base support 45. The cover 30 includes a small opening 29a adapted to the size of laboratory animals such that animals may be placed into the container or removed from the container through the opening 29a while the cover 30 is in place. The opening 29a provides a means for moving animals to and from the cage 27 without having to remove the entire cover 30 from the container. In this way, the release of gas from the cage 27 is reduced as animals are moved to and from the container. The opening 29a is adapted to receive a lid 31 which is complementary to the opening. Preferably, the lid 31 conforms to the perimeter of the opening 29a in sealing engagement to minimize the entry or release of gases to or from the container. The anesthetic host cage 27 may further include one or more partitions to subdivide the cage into a plurality of smaller compartments.

Anesthetic gas mix is delivered to anesthetic host cage 27 via an inlet 24. Referring to FIG. 8, an inlet 24 passes through the cover 30 of the host cage 27. The inlet 24 may alternatively pass through the sidewall 28 of the host cage. The inlet 24 is configured to cooperate with a quick-connect fitting 23. The quick-connect fitting allows laboratory personnel to attach and detach alternative conduits that deliver anesthetic gas, pure oxygen, or a combination of the two components to the anesthesia host cage 27.

The host cage 27 is configured to discharge exhaled gas from the interior of the cage as new gas is introduced into the cage. Removal of exhaust gases from the host cage 27 and the surrounding work area protects laboratory personnel from the adverse effects of inhaling anesthetic gas components. Referring to FIG. 8, the host cage 27 is shown with an outlet 25 configured to receive and remove exhaust gas from the interior of the cage. An air filter 29 may be mounted on the outlet 25, similar to the filter 17 attached to the solo apparatus 90 discussed earlier. Air filter 29 is configured to capture anesthetic gas contaminants, such as excess anesthetic gas mix and exhaled carbon dioxide as they are discharged from the host cage 27. The outlet 25 may release exhaust gas to the exterior of the host cage 27 where it is captured by a fume hood or other exhaust removal system in the laboratory facility. Alternatively, the outlet 25 may be connected directly to the facility's exhaust system via a conduit to facilitate removal of exhaust gases. Where conduit is used to connect the outlet 28 directly to the facility exhaust system, it may not be desirable or necessary to include a filter on the outlet, unless it is desired to monitor the content of contaminants in the gas discharged from the container. In such case a filter having a sensor may be used as described hereinafter.

The present system 1 may have a thermoregulatory system to control the body temperature of laboratory animals being anesthetized. The thermoregulatory system may be used in connection with one or more solo apparatuses 90 and/or a group apparatuses 92 at one time. Where a thermoregulatory system is used, the support bases 43 and 45 are comprised of hollow containers, as best shown in FIG. 7. The hollow bases 43 and 45 are formed of a heat conductive material. A heat-exchange medium in the bases 43 and 45 may be used to transfer heat by radiation or conduction through the walls of the base to the animal or animals placed on the base. A variety of heat-exchange media may be used in accordance with the present invention. It may be desirable to use water as the heat-exchange medium based on the low cost and general availability of water in laboratory facilities.

Preferably, the bases 43 and 45 are heated by circulating a fluid heat-exchange medium, such as water, through the bases to provide a substantially constant base temperature. Referring to FIGS. 5–7, the bases may comprise an inlet 98 adapted to receive heated water and an outlet 99 configured to discharge heated water from the hollow base. In the base 43 shown in FIG. 7, a longitudinal baffle 43c is provided along the longitudinal centerline of the base to assure longitudinal flow of heat exchange medium through the length of the base 43. The direction of flow of heater water is represented by the arrows 43d, 43e and 43f in FIGS. 5–7. The system 1 may utilize a variety of hydraulic elements and piping configurations, including flow-through systems and closed-loop pressurized systems. Referring to FIG. 1, a solo apparatus 90 and group apparatus 92 are shown connected in series in a closed loop heating system, but the apparatuses may alternatively be connected in parallel in a closed loop system. Where there is an ample supply of hot water, the apparatuses may be connected in an open system in which the hot water may flow through the apparatus and be discharged to waste. In the closed loop system shown in the drawings, a pump 47 is connected to the bases through a network of conduits to recirculate heated water through the bases. The pump 47 may comprise an internal reservoir having a heating element (not shown) connected to an electrical power supply through a power cord 47c. The electrical heating element may be submerged in the reservoir of the pump, and be energized to heat to the water under the control of a thermostat 47a as it flows through the pump 47. The pump 47 discharges the heated water to an influent line 42 where it begins circulating through the system apparatuses. In particular, the influent line 42 connects to an inlet port 44 on support base 45 to discharge heated water into the base. A first discharge line 48 connects to an outlet port 46 on the base 45 and is configured to receive water as it is cycled through the base. Line 48 connects to an inlet port 49 on support base 43 on the solo apparatus 90. As such, line 48 is configured to transfer heated water from base 45 to base 43. A second discharge line 59 connects to an outlet port 51 on the base 43 and returns the water back to the pump 47 where the water is reheated and recirculated. The thermoregulatory system is configured to maintain a desired body temperature of laboratory animals undergoing procedures on the bases 43 and 45 to ensure the viability of the animal and facilitate the successful completion of the procedure. Preferably, the pump 47 contains an adjustable thermostat 47a configured to control the temperature of the water in the thermoregulatory system in accordance with the physical requirements of the particular species of laboratory animal being treated. For example, the thermostat 47a may be operable to shut off the internal heating element when the temperature of water entering the pump reaches a particular temperature. A shut off switch 47b is provided to cut off power to the pump.

Referring now to FIGS. 10–14, the group apparatus 92 preferably includes an exhaust system 60 that removes exhaust gases and other gas releases from system elements to ensure the safety of laboratory personnel. The exhaust system 60 comprises a horizontal negative pressure recapture system. The exhaust system 60 comprises a plurality of stainless steel trays 61 that are covered by removable perforated steel grids 63. The grid is spaced above the bottom of the tray to provide a compartment which forms a plenum. The grids 63 are configured to support one or more of the solo apparatuses 90 and the group apparatuses 92 during use. The trays 61 are connected to an exhaust manifold 67 by exhaust conduits 65. The exhaust conduits 65 and manifold 67 are further connected to an exhaust fan or other mechanism within the facility's ventilation system that is operable to generate a negative pressure or vacuum in the plenum, the conduits and the manifold. As such, the trays 61 are configured to withdraw exhaust gases from the apparatuses 90, 92 when a negative pressure or vacuum is supplied to the conduits and plenum. Exhaust gases are withdrawn through the grids 63 and conduits where they are discharged from the manifold 67. Manifold 67 may comprise one or more filters, such as HEPA filters, to cleanse the air prior to its release into the general environment.

Figure 10:
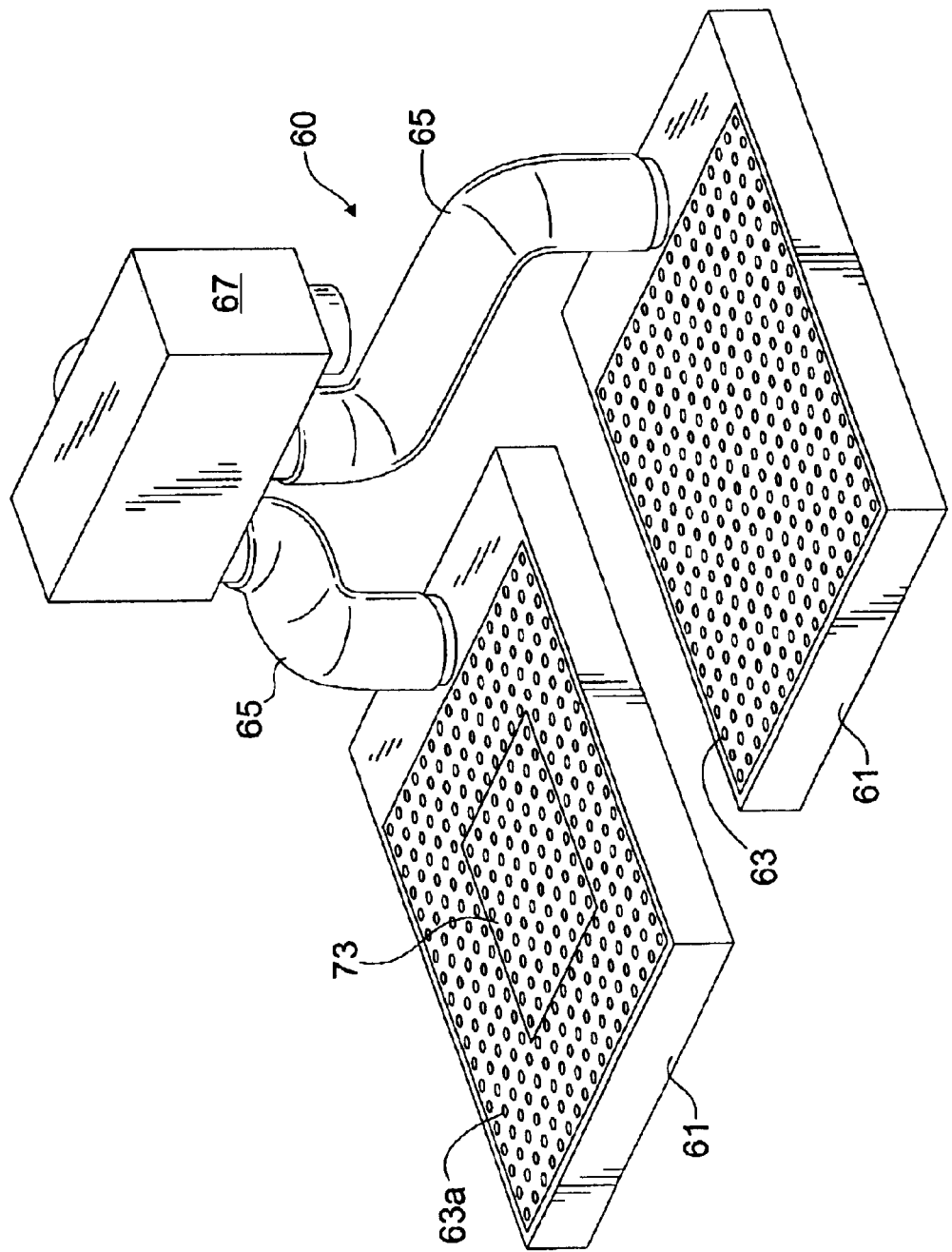
FIG. 10 is a perspective view of the front of an exhaust system, showing two embodiments of a perforated grid, manifold conduits and an exhaust manifold.
Figure 12:
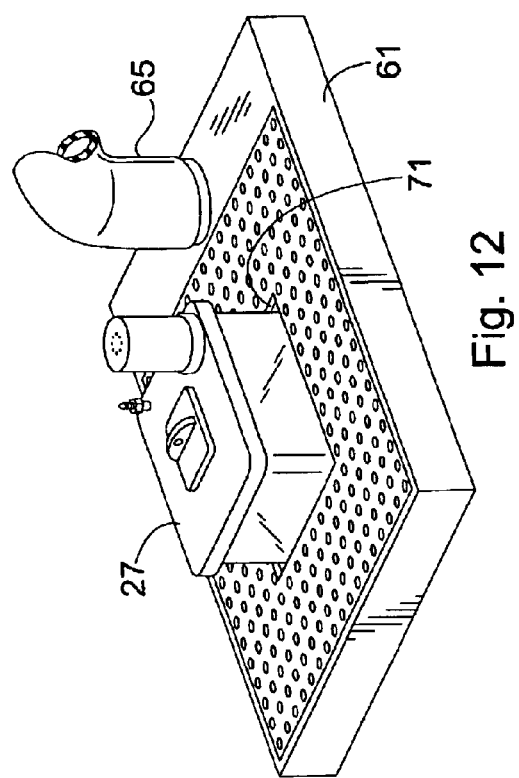
FIG. 12 is an assembled view of the perforated grid shown in FIG. 11.
Figure 11:
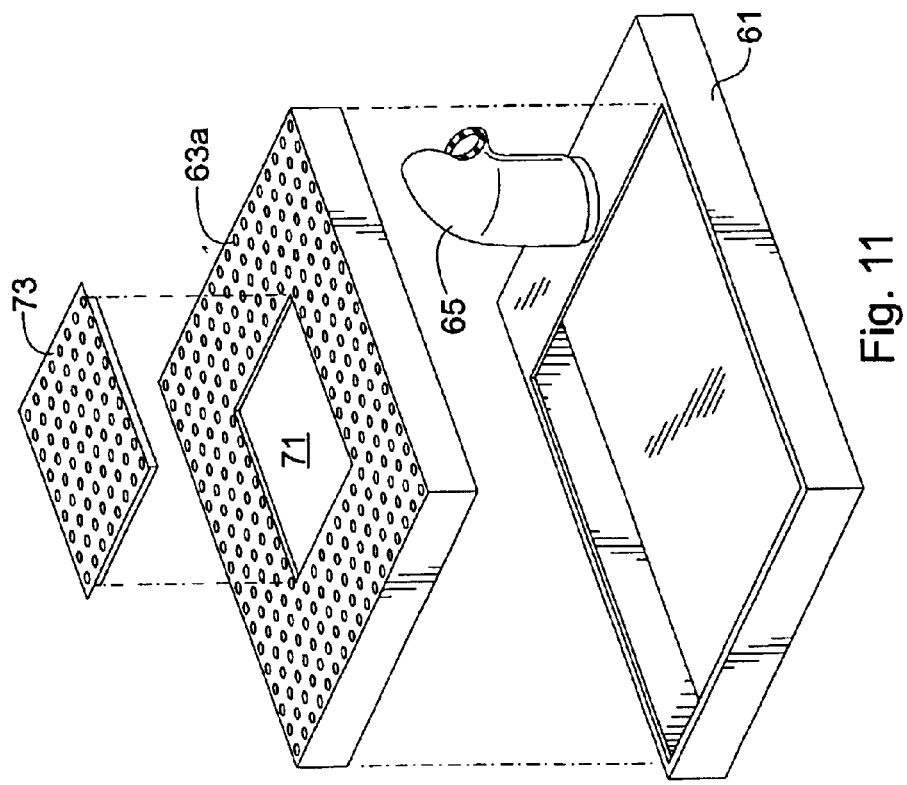
FIG. 11 is an exploded view of one embodiment of the perforated grid having a removable insert exposing an opening into which an anesthetic host cage may be inserted.
Figure 13:
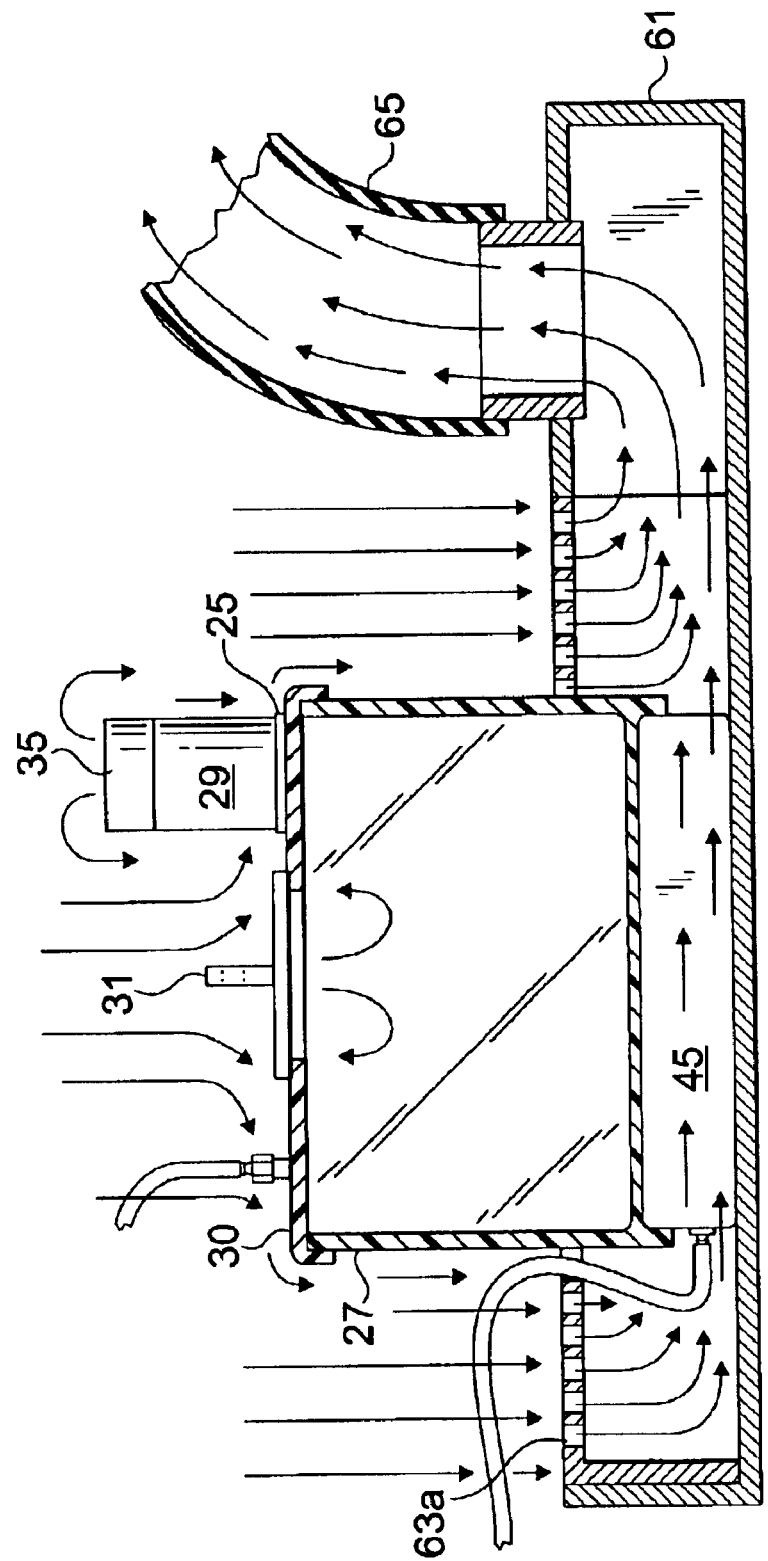
FIG. 13 is a cross sectional view of the perforated grid of FIG. 12 showing flow patterns during operation of the exhaust system.
Figure 14:
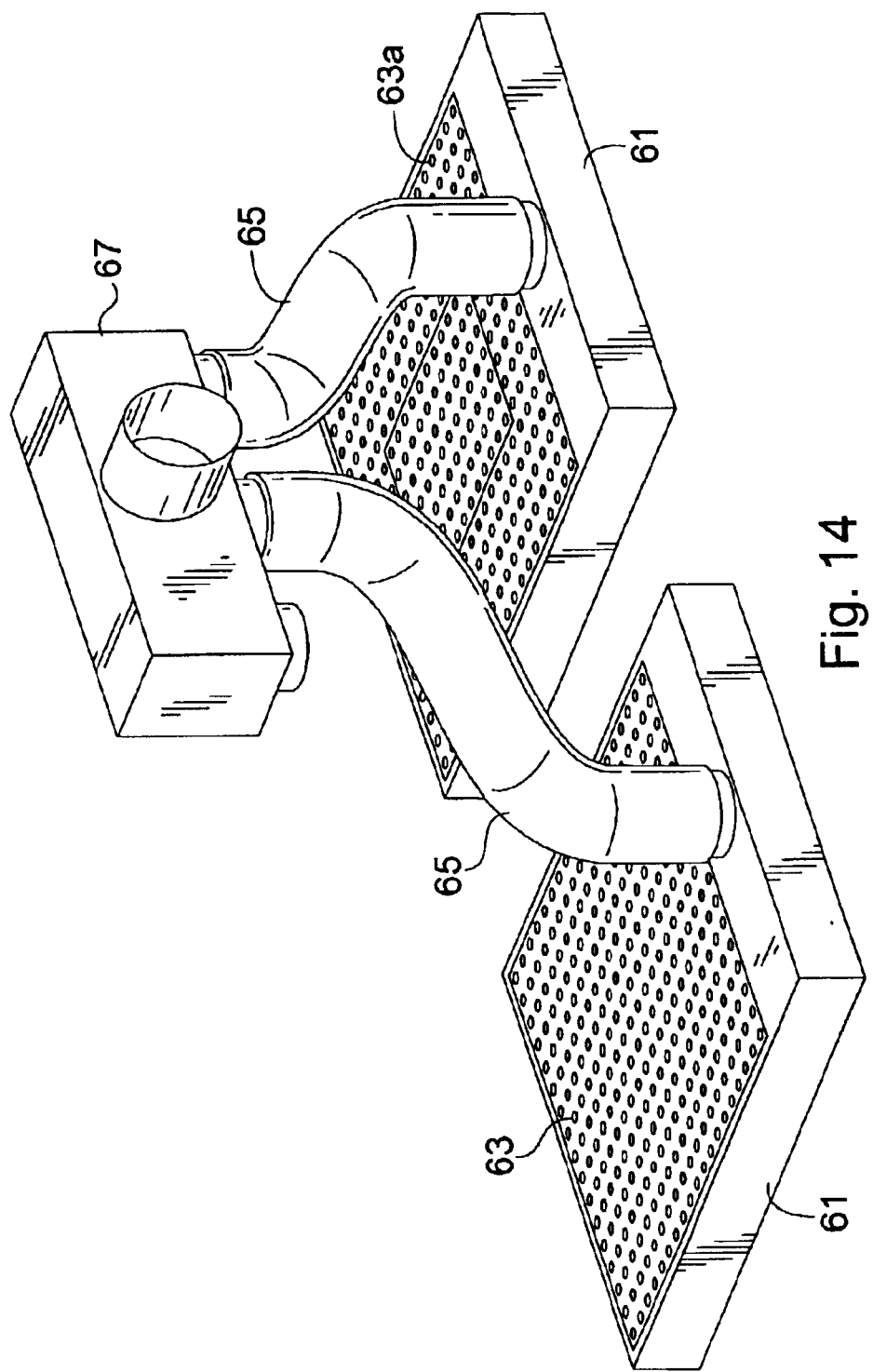
FIG. 14 is a schematic view of the back of the Exhaust System including a perforated grid, manifold conduit, manifold and attachment thereto.

When anesthetic gas is delivered to a group apparatus 92, an alternate grid structure 63a may be used with the exhaust system 60, as shown best in FIGS. 10–12. Grid 63a comprises a centrally located cut out 71 adapted to receive an anesthetic host cage 27. In particular, the perimeter of the cut out 71 is slightly larger than the exterior perimeter of the anesthetic host cage 27 such that the host cage may be partially inserted into the cut out and extend into the tray 61, as shown in FIG. 12. The support base 45 for the host cage 27 may be placed in the tray 61 beneath the cut out 71 to support the host cage, as shown in FIG. 13. By positioning the host cage 27 through the grid 63a in this manner, the required overhead space for the group apparatus 92 is reduced, and the removal of exhaust gases from the host cage 27 is facilitated, as indicated by the plurality of arrows in FIG. 13. Exhaust gases in the host cage 27 exit the cage through the outlet 25 and outlet filter 29. Vacuum pressure supplied through the exhaust conduit 65 creates negative pressure in the tray 61. The negative pressure in the tray 61 causes the exhaust gases to wash past the sides of the container 27, through the grid 63a and into the tray. The exhaust gases are then drawn up through the exhaust conduit 65, as indicated by the arrows in FIG. 13.

Referring to FIG. 11, a cover plate 73 may be provided for placement over the cut out 71 when a the cut out is not in use. The cut out 71 is configured to receive and support the cover plate 73 in a position such that the top surface of the cover plate is generally flush with the surface of the grid 63a to provide a uniform and substantially uninterrupted grid surface.

In some applications, it may be necessary to discontinue anesthetic gas mix and deliver pure oxygen to the laboratory animal. Pure oxygen is used, for example, to facilitate rapid recovery of an animal after anesthetic gas has been applied. Referring to FIG. 2, an emergency bypass is provided in the system 1 to deliver pure oxygen directly to one or more apparatuses in the system. The oxygen supply 2 includes an emergency bypass junction that connects to a bypass manifold 4. The bypass manifold 4 has an outlet connected to a conduit 41 which connects to one or more apparatuses of the present system. In FIG. 2, the conduit 41 provides an emergency bypass line to a group apparatus 92. Preferably, the conduit 41 has a quick-connect fitting at its remote end which cooperates with compatible fittings on the apparatuses of the system 1 so that the bypass conduit can be readily connected and disconnected to different apparatuses as needed.

Referring to FIG. 3, an attachment 35 may be provided at the discharge end of the filters 17 and 29 to monitor the condition of the filters. More specifically, an attachment 35 may be connected to filters 17 and 29 to measure the concentration of anesthetic component or other contaminants being released through the filter. When the concentration of discharged contaminants exceeds a pre-established safety limit, such as a limit based on federal regulations or OSHA standards, the sensor may send an electronic signal to trigger a visual or an audible or a combined visual and auditory signal indicating that a filter is not operating adequately and should be serviced, or the anesthetic flow regulator requires attention. Preferably, the absorbent material in filters 17 and 29 are packaged in replaceable cartridges, which are easily loaded into and unloaded from filter canisters. In this way, a spent filter cartridge or improperly working filter cartridge may be easily removed and replaced with a new filter.

Figure 16:
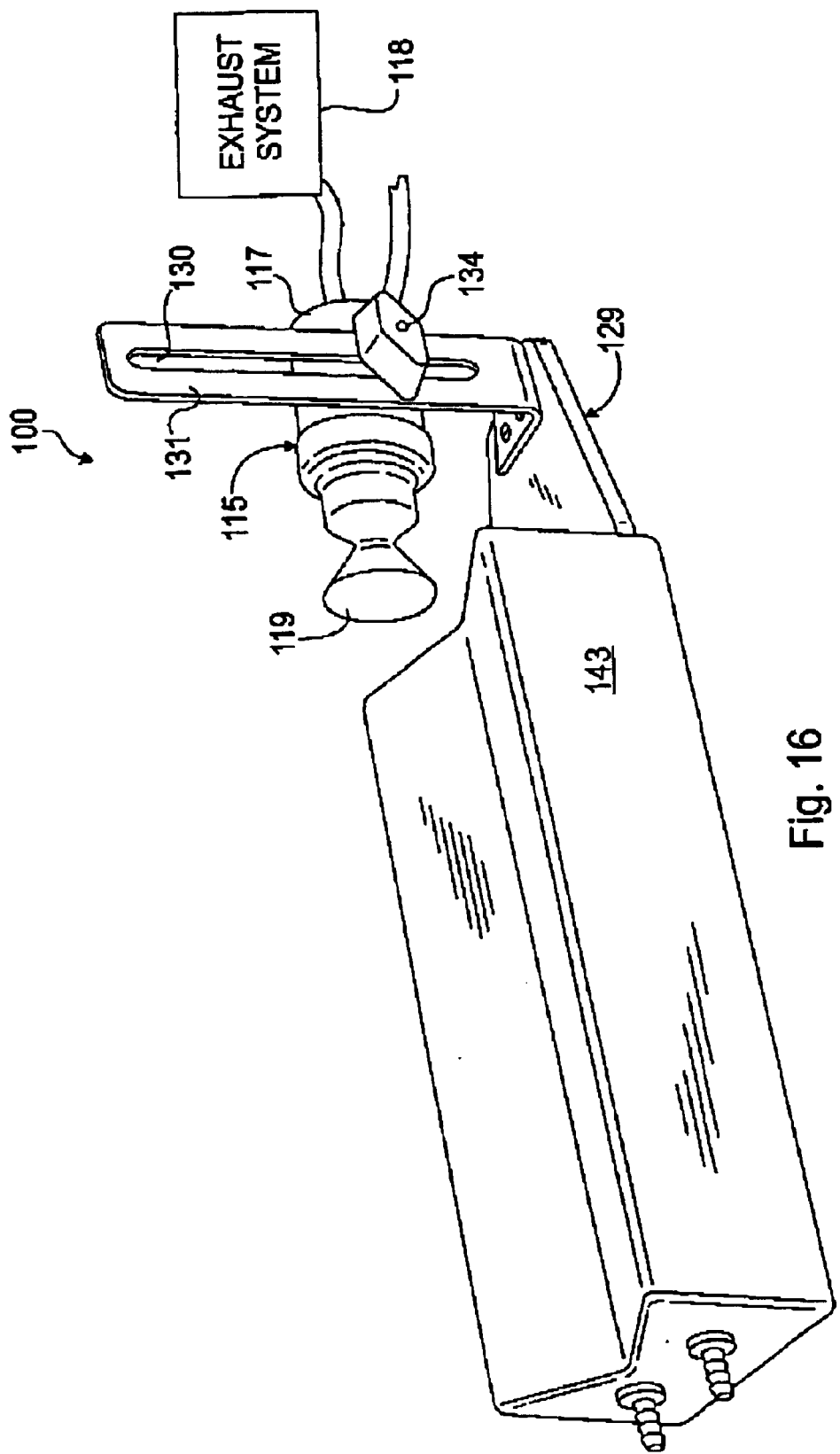
FIG. 16 is a perspective view of an alternate gas delivery system which includes a non-rebreathing gas delivery mask and an air exchange chamber.

Referring now to FIG. 16, the present invention further provides a portable anesthetizing system 100 for anesthetizing laboratory animals. The portable anesthetizing system 100 comprises elements that are similar to the solo apparatuses 90 discussed earlier, and may replace one of the solo apparatuses of FIG. 2, and may have a quick-connect fitting which may be readily directly connected to the vaporizer 9, or the gas supply 2. The portable system 100 comprises a breathing device 115 connected to a support base 143. Like the support base 43 in the solo apparatus 90, the support base 143 in the portable system may have a number of geometric configurations and connect to a thermoregulatory system for controlling the body temperature of an animal placed on the base. The breathing device 115 comprises a non-rebreathing gas delivery mask 119 attached to a breather chamber or shroud 117. The shroud 117 preferably has outer dimensions which are the same as as the outside dimensions of the connector 16a of the chamber 16, so that the shroud may accept any one of the masks 78, 178 and 278. The breather shroud 117 is linked, in turn, to an exhaust system 118. Breather shroud 117 may discharge through an absorbent filter media in the shroud to remove contaminants from the exhaust gas.

Figure 17:
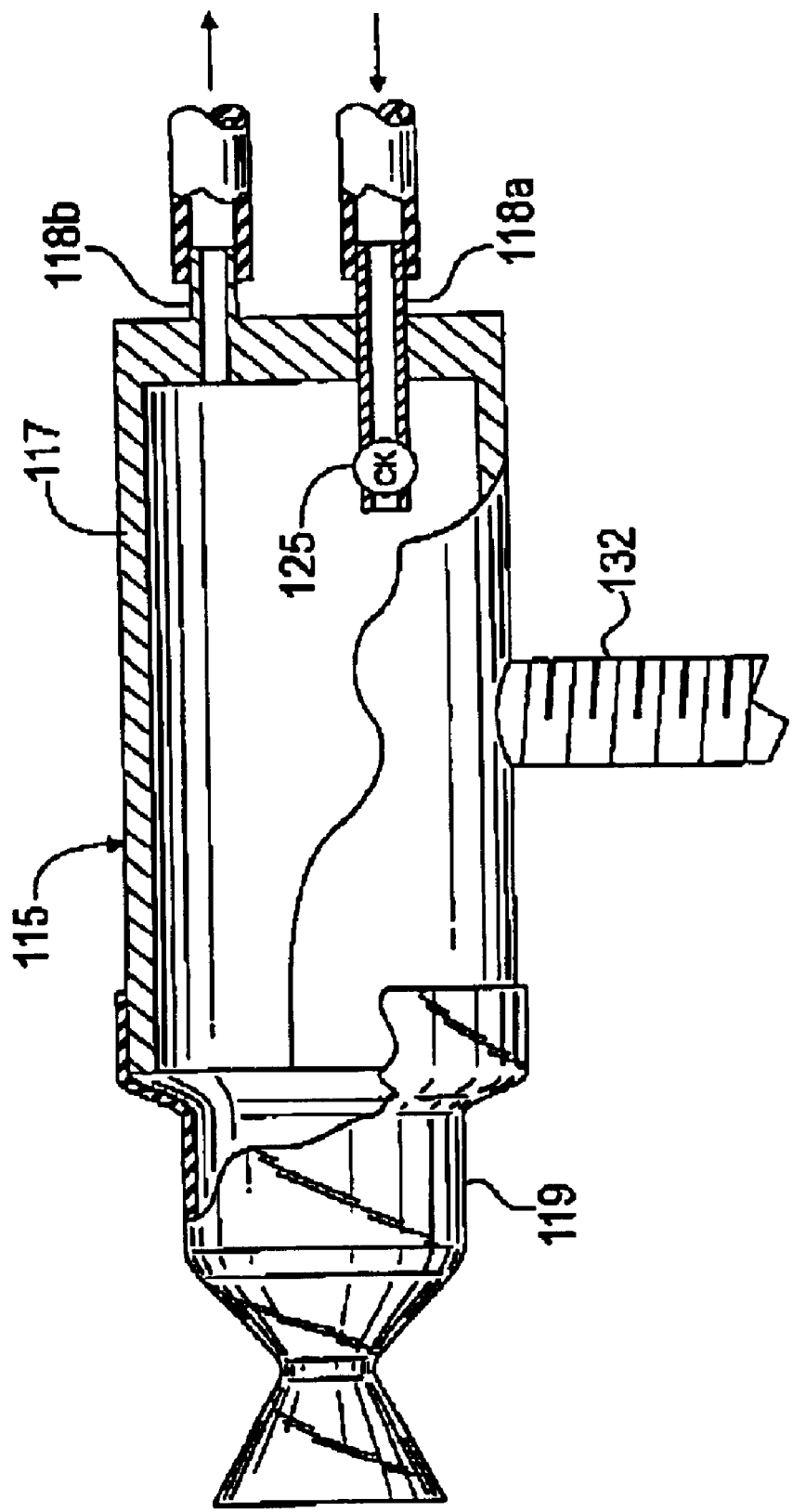
FIG. 17 is a view of the air exchange chamber of FIG. 16 with parts broken away to illustrate its construction.

Referring now to FIG. 17, internal elements of the portable breathing device 115 are illustrated. The shroud 117 comprises an inlet port 118a through which anesthetic gas is delivered, and an outlet port 118b through which gas is discharged. A check valve 125 is connected in line with the inlet port 118a to limit the flow of anesthetic gas into the shroud 117. In particular, the check valve 125 is operable in an open position when the laboratory animal inhales and creates a vacuum pressure in the shroud 117. When the animal stops inhalation, the check valve 125 closes to limit further entry and accumulation of anesthetic gas in the shroud 117. Excess gas and any exhausted gas that reenters the shroud are discharged through the outlet port 118b. The outlet port 118b may be connected to the exhaust system 60 described earlier, which may or may not include filter canisters and filter sensors. In addition, the shroud 117 may be connected to an emergency bypass system as described earlier to supply pure oxygen to the animal. A ventilator bulb similar to the ventilator 21 shown in FIGS. 1 and 3 may be provided to manually ventilate the portable breathing device 115 during resuscitation of a laboratory animal.

Portable breathing device 115 may be mounted on a support structure 129, as shown in FIG. 16. The support structure 129 provides means to position the gas delivery mask 119 relative to the position of the nose of an animal placed on the portable support base 143. The support structure 129 is comprised of a stand 131 which includes a generally vertical slot 130 and an adjusting nut 134 which cooperates with a threaded stud 132 projecting from the shroud 117 and inserted through the slot. As such, the stud 132 cooperates with the nut 134 to hold the shroud and stand together in frictional engagement. The adjusting nut 134 may be tightened on the stud 132 to fix the delivery mask 119 in a position above the the base 143 to accommodates the particular species of laboratory animal undergoing treatment. The adjusting nut 134 may be loosened on the stud 132 so that the stud is free to slide along the vertical slot 130 in the stand. By sliding the stud in the slot, the breathing device 115 is vertically displaceable to permit adjustment of the mask 119 relative to the animal support base 143. Frictional engagement between the nut 134 and the side of the stand is sufficie 209 o hold the mask in the desired position.

Figure 18:
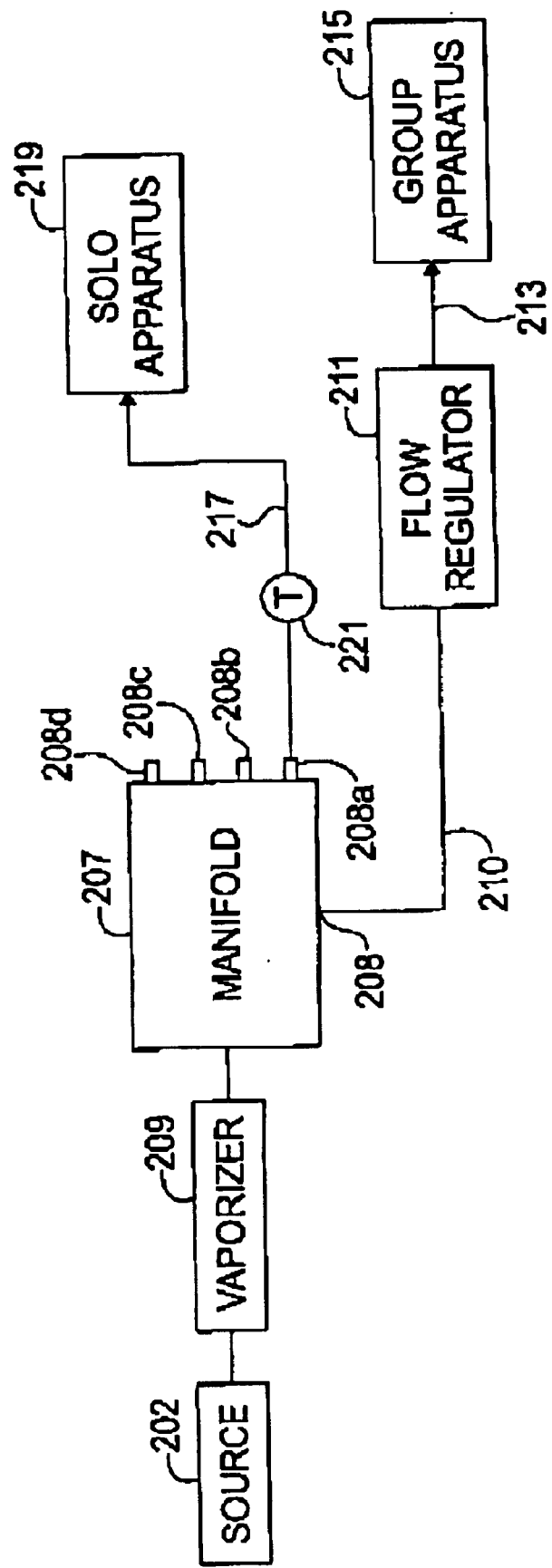
FIG. 18 is a block diagram of a preferred arrangement of connections to the group and solo apparatuses.

It has been found desirable to use separate gas pressures to the group apparatus or apparatuses on one hand and the solo apparatus or apparatuses on the other hand. To this end the system of FIGS. 1–3 is modified as shown in FIG. 18. In this figure, a source 202 of carrier gas is connected to a vaporizer 209 which introduces anesthetizing components to the stream of carrier gas prior to its feed into a manifold 207. In a typical installation, the supply of gas to the manifold 207 is at a pressure of 10–12 mm Hg. The manifold has a single port 208 which is adapted to be connected to a large conduit 210 leading to a flow regulator 211 which, through an output conduit 213, will output an anesthetizing gas stream regulated in accordance with the demand of the animals in a group apparatus 215 at the desired pressure of up to 12 mm. Hg. The manifold 207 additionally has multiple ports 208a through 208d each of which is adapted to be connected to a small conduit 217 which is connected to a selected solo apparatus 219. When the flow regulator is fully open, the pressure in the manifold will drop to 6 mm.Hg. When the flow is reduced to 100 ml/min, the manifold pressure returns to about 12 mm.Hg, which is applied to the group apparatus conduit 215. In each case, the port 208a and the small conduit 217 throttles the flow and reduces the pressure of the gas mixture in the solo apparatus to less then one-fifth of the pressure in the manifold, preferably less than 1 mm Hg. If the small conduit 217 does not provide the desired pressure reduction, an optional throttle valve 221 may be interposed in the conduit 217 to attain the desired pressure in the solo apparatus. By using a reduced pressure in the solo apparatus, the check valve, as described above at 125, will operate to prevent rebreathing of the contaminants exhaled by the animal through the mask associated with the solo apparatus.

The terms and expressions which have been employed are used as terms of description and not of limitation. There is no intention in the use of such terms and expressions of excluding any equivalents of the features shown and described or portions thereof. It is recognized, therefore, that various modifications are possible within the scope and spirit of the invention. Accordingly, the invention incorporates variations that fall within the scope of the following claims.

We claim:

1. An apparatus for anesthetizing a first laboratory animal having a breathing passage, the apparatus, comprising:
   a source of a pressurized gas;
   a vaporizer fluidly connected to said source and adapted to introduce an anesthetic component into the pressurized gas stream to create an anesthetic gas mixture;
   a manifold connected to said vaporizer receiving said gas mixture and having multiple outlet ports operable to deliver the gas mixture through said ports simultaneously;
   a first breathing device connected to a first of said outlet ports, said first breathing device comprising a shroud forming an air-exchange chamber for transferring gas to and from the first animal's breathing passage, said shroud comprising an inlet port for permitting gas to flow into the chamber, and an exhaust port for permitting gas to evacuate the chamber; and
   a check valve connected with the inlet port and extending within the shroud in operable communication with the animal's breathing passage, said check valve being operable in an open position only when the first animal inhales to permit anesthetic gas mixture to flow into the chamber, and in a closed position when the first animal exhales to prevent the anesthetic gas mixture from entering the chamber,
   wherein said exhaust port is operable to evacuate substantially all exhaust and accumulated gas from the chamber when the check valve is in the closed position to minimize the animal's re-inhailing of carbon-dioxide and anesthetic gas mixture exhaled into the chamber.

2. The apparatus of claim 1 comprising a second breathing device connected to a second of said outlet ports and configured to deliver the gas mixture to a second animal.

3. The apparatus of claim 2 wherein the second breathing device comprises an imperforate container having a substantially sealed environment adapted to enclose one or more animals, said container having an inlet to introduce the gas mixture into the sealed environment for inhalation by the animal or animals.

4. The apparatus of claim 3 comprising an animal support base and a thermoregulatory system for transferring heat to the exterior of the support base, and wherein the container has a pocket configured to fit snugly over the support base to enable heat transfer from the base to the container.

5. The apparatus of claim 4 wherein the container has an opening adapted to permit passage of an animal to and from the container, and a lid configured for placement over the opening to maintain said sealed environment for receiving the gas mixture.

6. The apparatus of claim 4 wherein the container has a container exhaust port to discharge gases exhaled by the one or more animals, and including a filter cartridge connected to said container exhaust port to filter out contaminants contained in the exhaled gases.

7. The apparatus of claim 3 wherein the container inlet comprises a check valve that controls the flow of the gas mixture into said sealed environment.

8. The apparatus of claim 2 comprising a bypass line connected to said source of pressurized gas, said bypass line being configured to deliver pressurized gas to one of said first and second breathing devices as a replacement for said gas mixture, said replacement gas having constituents for enabling rapid recovery of the animal from the effects of the gas mixture upon the animal.

9. The apparatus of claim 1 comprising a thermoregulatory system adapted to maintain the body temperature of the first animal, said thermoregulatory system comprising a base configured to support the first animal in a position to receive the gas mixture delivered by the first breathing device, a supply of fluid heat exchange medium, a circulator, and an inlet and an outlet in said base to circulate said heat exchange medium through said base to transfer heat to the exterior of said base and to the animal supported by said support.

10. The apparatus of claim 9 wherein the circulator comprises a pump having a reservoir for the fluid heat exchange medium, and a heating element in said reservoir, said heating element being configured to heat the fluid media, and said pump being configured to circulate the heated fluid medium through said inlet and said outlet.

11. The apparatus of claim 10 wherein said inlet and outlet are connected in a closed loop to said pump reservoir whereby said fluid medium is recirculated in said closed loop from said pump, through said base and back to said pump.

12. The apparatus of claim 1 wherein the first breathing device comprises a plurality of masks, each mask having one end configured to conform to the anatomy of a different animal, and a second end adapted to connect to said chamber, such that when one of said masks is connected to said chamber, gas in said chamber is delivered to the nose of the animal; said chamber having a filter cartridge connected to said exhaust port.

13. The apparatus of claim 12 wherein the second end of each of said plurality of masks is the same as the second end of the others of said plurality of masks to enable substitution of one mask for another.

14. The apparatus of claim 12 wherein the chamber is configured to receive gases exhaled by the animal through the mask, said check valve enabling the flow of the gas mixture into the chamber for delivery to the animal, and preventing reverse flow of the exhaled gases.

15. The apparatus of claim 14 including a filter cartridge connected to said exhaust port to filter out contaminants contained in the exhaled gases.

16. The apparatus of claim 15 wherein said filter cartridge includes a sensor to sense the condition of the gases passing through the cartridge, said sensor including an indicator to signal when the condition of the gases makes it desirable to service the filter.

17. The apparatus of claim 1 comprising an exhaust system configured to remove gas emissions generated in the first breathing device, said system comprising a filter cartridge having an inflow end connected to said first breathing device, a filter media within said cartridge adapted to remove contaminants in the gas emissions, an indicator that monitors the absorptive capacity of the filter media and generates a warning signal which corresponds to the condition of the filter media, said signal comprising at least one of an auditory signal and a visual signal.

18. The apparatus of claim 17 wherein said filter cartridge has an effluent end, said apparatus including a housing coupled to the effluent end of the cartridge, said housing supporting said indicator, said indicator including a sensor adapted to transmit an electronic warning signal when the sensor detects a concentration of contaminants in excess of a selected level, and a signaling device to generate said auditory or visual signal when said sensor transmits the electronic signal.

19. An apparatus for anesthetizing one or more laboratory animals having a respiratory system, the apparatus comprising:
   a source of a pressurized gas;
   a vaporizer fluidly connected to said source and adapted to introduce an anesthetic component into the pressurized gas stream to create an anesthetic gas mixture;
   a manifold connected to said vaporizer receiving said gas mixture and having multiple outlet ports operable to deliver the gas mixture through said ports simultaneously;
   a first animal support having a first breathing device connected to a first of said outlet ports and configured to deliver the gas mixture to an animal's respiratory system;
   a second animal support having a second breathing device connected to a second of said outlet ports and configured to deliver the gas mixture to an animal's respiratory system;
   a thermoregulatory system for each of said animal supports adapted to control the temperature of its associated support to maintain the body temperature of an animal supported by said support at a selected temperature; and
   an exhaust system comprising a negative pressure recapture system, said recapture system including a perforated grid, a tray having a bottom surface and configured to support the grid in a substantially horizontal position above said surface to provide a plenum, one or more conduits connected to said plenum, and means for generating negative pressure in the plenum and conduits, at least one of said animal supports being disposed adjacent said perforated grid, whereby the negative pressure draws gas emissions into said plenum from around said adjacent animal support.

20. The apparatus of claim 19 wherein said grid has an opening conforming to the outline of said adjacent animal support, aid support being positioned within said opening whereby the grid surrounding said adjacent support creates a flow of ambient air into said plenum around the perimeter of said adjacent animal support, said ambient air entraining gas emissions from said adjacent animal support.

21. An apparatus for anesthetizing a laboratory test animal having a breathing passage, the apparatus, comprising:
   a source of an anesthetic gas mixture;
   a breathing device having a fluid connection to said source to deliver the gas mixture to the breathing passage, said breathing device comprising a base configured to support the test animal in a position to receive the gas mixture;
   a thermoregulatory system adapted to control the temperature of said base to maintain the body temperature of the test animal supported by said base at a selected temperature, said thermoregulatory system including a supply of fluid heat exchange medium, a circulator, and an inlet and an outlet in said base to circulate said heat exchange medium through said base to transfer heat to the exterior of said base and to the test animal;

said breathing device comprising a shroud that forms an air exchange chamber and a plurality of masks, each mask having one end configured to conform to the anatomy of a different animal, and a second end adapted to connect to said chamber, such that when one of said masks is connected to said chamber gas in said chamber is delivered to the nose of the animal through said one mask, and exhaled gases of the test animal are discharged into said chamber, said chamber having a chamber inlet and a chamber outlet;

a check valve connected with the chamber inlet and extending within the shroud in operable communication with the test animal's breathing passage, said check valve being operable in an open position only when the test animal inhales to permit anesthetic gas mixture to flow into the chamber, and in a closed position when the test animal exhales to prevent the anesthetic gas mixture from entering the chamber, wherein said chamber outlet is configured to evacuate substantially all exhaust and accumulated gas from the chamber when the check valve is in the closed position to minimize the animal's re-inhailing of carbon-dioxide and anesthetic gas mixture exhaled into the chamber.

22. The apparatus of claim 21 wherein the second end of each of said plurality of masks is the same as the second end of the others of said plurality of masks to enable substitution of another mask for said one mask.

23. The apparatus of claim 21 including a filter cartridge connected to said chamber outlet to filter out contaminants contained in the exhaled gases, said cartridge including a sensor to sense the condition of the gases passing through the cartridge, and an indicator to signal when the condition of the gases makes it desirable to service the filter.

24. An apparatus for anesthetizing a laboratory test animal having a respiratory system, the apparatus, comprising:

a source of an anesthetic gas mixture;

an animal support for the test animal having a breathing device having a fluid connection to said source to deliver the gas mixture to an animal's respiratory system, said animal support comprising a base configured to support the test animal in a position to receive the gas mixture; and a thermoregulatory system for said animal support adapted to control the temperature of said base to maintain the body temperature of the test animal supported by said base at a selected temperature, said thermoregulatory system including a supply of fluid heat exchange medium, a circulator, and an inlet and an outlet in said base to circulate said heat exchange medium through said base to transfer heat to the exterior of said base and to the test animal;

said breathing device comprising an air exchange chamber and a plurality of masks, each mask having one end configured to conform to the anatomy of a different animal, and a second end adapted to connect to said chamber, such that when one of said masks is connected to said chamber, gas in said chamber is delivered to the nose of the animal through said one mask, and exhaled gases of the test animal are discharged into said chamber, said chamber having a chamber outlet, said fluid connection including a check valve to allow unidirectional flow of the gas mixture into said chamber, said check valve enabling the flow of the gas mixture into the chamber for delivery to the test animal, and preventing reverse flow of exhaled gases through said connection, and causing said exhaled gases to flow through said chamber outlet, wherein said animal support base has a hollow interior connected to said thermoregulatory system, and a channeled first side and a flat second side, providing alternate areas for supporting the test animal.

25. An apparatus for anesthetizing one or more laboratory animals having a respiratory system, the apparatus, comprising:

a source of a pressurized gas;

a vaporizer fluidly connected to said source and adapted to introduce an anesthetic component into the pressurized gas stream to create an anesthetic gas mixture;

a manifold connected to said vaporizer receiving said gas mixture and having multiple outlet ports operable to deliver the gas mixture through said ports simultaneously;

a first animal support having a first breathing device connected to a first of said outlet ports and configured to deliver the gas mixture to an animal's respiratory system, said first breathing device comprising an air exchange chamber and a mask having one end configured to conform to the anatomy of a test animal, and a second end adapted to connect to said chamber, such that gas in said chamber is delivered to the nose of the animal; said chamber having a fluid connection to one of said outlet ports, said fluid connection including a check valve to allow unidirectional flow of the gas mixture into said chamber, said fluid connections throttling the unidirectional flow from said manifold to maintain the pressure of the gas mixture in said chamber below 1 mm.Hg; and a second animal support having a second breathing device connected to a second of said outlet ports and configured to deliver the gas mixture to an animal's respiratory system, said second breathing device comprising an imperforate container having a substantially sealed environment adapted to enclose one or more animals, said container having an inlet to introduce the gas mixture into the sealed environment for inhalation by the animal or animals, and fluid connections including a flow regulator connected to said manifold to afford flow of the gas mixture from said manifold into said container, said manifold receiving the gas mixture at a pressure at least five times greater than the pressure of the gas mixture in said chamber of the first breathing device.

26. The apparatus of claim 25 wherein said first breathing device comprises a plurality of masks, each mask having one end configured to conform to the anatomy of a different animal, and a second end adapted to connect to said chamber, the second end of each of said plurality of masks being the same as the second end of the others of said plurality of masks to enable substitution of one mask for another.

27. The apparatus of claim 25 wherein said chamber is configured to receive gases exhaled by the animal through the mask, said check valve enabling the flow of the gas mixture into the chamber for delivery to the animal, and preventing reverse flow of the exhaled gases, said chamber having an exhaust port to discharge gases exhaled by the animal, and including a filter cartridge connected to said exhaust port to filter out contaminants contained in the exhaled gases.

28. The apparatus of claim 27 wherein said filter cartridge includes a sensor to sense the condition of the gases passing through the cartridge, said sensor including an indicator to signal when the condition of the gases makes it desirable to service the filter.

29. A method of anesthetizing laboratory animals, comprising the steps of providing an animal support having a hollow base with a channeled first side and a flat second side, and placing a live test animal having a functioning respiratory system on a given one of the first and second sides of the animal support, providing a delivery system for delivering an anesthetic gas mixture to the animal's respiratory system;

regulating the test animal's body temperature condition during the delivery of the anesthetic compound by circulating heat exchange medium through said hollow base, and transferring heat from said heat exchange medium to the animal through said given side of the animal support; and capturing gases exhaled by the animal's respiratory system.

30. The method of claim 29 wherein the given side is the flat side of the base, and including the further steps of performing a test procedure on the animal after it is anesthetized, and following performance of the test procedure, transferring the animal to the channeled side of the base.

31. A method of anesthetizing a plurality of laboratory animals, comprising the steps of providing a solo animal support apparatus having a hollow base and a mask, and placing a live test animal having a functioning respiratory system on the hollow base with its respiratory system open to the interior of the mask, providing a laboratory enclosure having a bottom to constitute a group animal support apparatus, and placing one or more live test animals in said enclosure, providing a delivery system for delivering an anesthetic gas mixture to the respiratory system of the animals through the mask in the solo apparatus and through said enclosure in the group apparatus;

maintaining the pressure of the gas mixture in the mask to less than 1 mm.Hg, and maintaining the pressure of the gas mixture in the enclosure in the range of 6 to 12 mm.Hg, regulating the test animal's body temperature condition during the delivery of the anesthetic compound by circulating heat exchange medium through the hollow base, and transferring heat from the heat exchange medium to the animal through the given side of the animal support; and capturing gases exhaled by the animal's respiratory system.

32. A method according to claim 31 including the steps of providing a second hollow base adjoining the bottom of the enclosure, and regulating the body temperature of the one or more test animals in the enclosure during the delivery of the anesthetic compound by circulating heat exchange medium through the second hollow base, and transferring heat from the heat exchange medium to the one or more animals through the bottom of the enclosure.

* * * * *